US006863891B2

(12) United States Patent
Engel et al.

(10) Patent No.: US 6,863,891 B2
(45) Date of Patent: *Mar. 8, 2005

(54) OLIGOPEPTIDE LYOPHILISATE, THEIR PREPARATION AND USE

(75) Inventors: Jürgen Engel, Alzenau (DE); Burkhard Wichert, Bielefeld (DE); Dieter Sauerbier, Werter (DE); Thomas Reissmann, Frankfurt am Main (DE)

(73) Assignee: Zentaris AG, Frankfurt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/040,457

(22) Filed: Jan. 9, 2002

(65) Prior Publication Data

US 2002/0103113 A1 Aug. 1, 2002

Related U.S. Application Data

(60) Division of application No. 08/468,145, filed on Jun. 6, 1995, which is a continuation-in-part of application No. 08/198,037, filed on Feb. 22, 1994, now abandoned.

(30) Foreign Application Priority Data

Feb. 19, 1993 (DE) .......................................... 43 05 225

(51) Int. Cl.⁷ ............................................. A61K 39/00
(52) U.S. Cl. ................................ 424/184.1; 424/184.1; 424/185.1; 424/193.1; 514/15; 514/14; 514/800; 514/255; 514/12; 514/13; 530/300; 530/313; 530/328; 930/110; 930/130
(58) Field of Search ........................... 424/184.1, 185.1, 424/193.1; 514/151.2, 141.3, 800, 255; 530/300, 313, 328; 930/110, 130

(56) References Cited

U.S. PATENT DOCUMENTS

| | | | |
|---|---|---|---|
| 3,816,386 A | | 6/1974 | Hedlund et al. |
| 4,372,884 A | | 2/1983 | Brown et al. |
| 4,512,923 A | | 4/1985 | Flegel et al. |
| 4,565,804 A | | 1/1986 | Rivier et al. |
| 4,693,993 A | | 9/1987 | Stewart et al. |
| 4,701,499 A | | 10/1987 | Kornreich et al. |
| 4,711,877 A | | 12/1987 | Moore |
| 4,716,242 A | | 12/1987 | Engel et al. |
| 4,800,191 A | * | 1/1989 | Schally et al. ................. 514/15 |
| 4,908,475 A | | 3/1990 | Callahan et al. |
| 5,198,533 A | | 3/1993 | Schally et al. |
| 5,204,335 A | | 4/1993 | Sauerbier et al. |
| 5,268,360 A | | 12/1993 | Yoshikawa et al. |
| 5,446,033 A | | 8/1995 | Engel et al. |
| 5,663,145 A | | 9/1997 | Engel et al. |
| 5,728,738 A | | 3/1998 | Engel et al. |
| 5,750,131 A | | 5/1998 | Wichert et al. |
| 5,773,032 A | * | 6/1998 | Engel et al. ................. 424/501 |
| 5,945,128 A | | 8/1999 | Deghenghi |
| 5,968,895 A | | 10/1999 | Gefter et al. |
| 5,998,377 A | | 12/1999 | Engel et al. |
| 6,022,860 A | | 2/2000 | Engel et al. |
| 6,054,555 A | | 4/2000 | Engel et al. |
| 6,106,805 A | * | 8/2000 | Engel et al. ................. 424/9.1 |
| 6,297,379 B1 | * | 10/2001 | Furuya et al. |
| 6,340,686 B1 | * | 1/2002 | Furuya et al. |
| 6,585,982 B1 | * | 7/2003 | Grondahl et al. ........... 424/400 |
| 6,627,609 B1 | * | 9/2003 | Bernd et al. ................. 514/15 |
| 6,635,740 B1 | * | 10/2003 | Enright et al. .............. 530/324 |
| 2001/0041672 A1 | * | 11/2001 | Stockemann et al |
| 2002/0198155 A1 | * | 12/2002 | Stockmann et al |
| 2003/0100509 A1 | * | 5/2003 | Sarlikiotis et al. ............ 514/15 |

FOREIGN PATENT DOCUMENTS

| | | | |
|---|---|---|---|
| DD | 141 996 | * | 6/1980 |
| EP | 0 175 506 | | 3/1986 |
| EP | 0 268 066 | | 5/1988 |
| EP | 0 277 829 | | 8/1988 |
| EP | 88-308573 | | 9/1988 |
| EP | 0 299 402 | | 1/1989 |
| JP | 61-87695 | | 5/1986 |
| JP | 63-201199 | | 8/1988 |
| JP | 05-000963 | | 10/1991 |
| JP | 64-034997 | | 6/1999 |
| WO | WO 91/13092 | | 9/1991 |
| WO | WO 91/16038 | | 10/1991 |
| WO | WO 91/19743 | | 12/1991 |

OTHER PUBLICATIONS

Reissmann et al, Human Reproduction, 1995, 10/8:1974–1981.*
Rongieres–Bertrand et al, Human Reproduction, 1999, 14/3:683–688.*
Ludwig et al, Arch. Gynecol. Obstet., 2000, 264:29–32.*
Niwa et al, J. Chromatography, 1999, 729:245–253.*
Albano et al, Fertility and Sterility, 1998, 70/2:357–359.*
Reissmann et al, J. Cancer Res. Clin. Oncol., 1992, 118:44–49.*
Albano et al, Human Reproduction, 1996, 11/10:2114–2118.*
Oliveness et al, Fertility and Sterility, 2000, 73/2:314–320.*
Tavaniotou et al, Human Reproduction, 2001, 16/4:663–667.*
Olivennes et al, Infertility and Reproductive Medicine Clinics of North America, 2001, 12/1:119–128.*
Albano et al, Human Reproduction, 2000, 15/3:526–531.*
Olivennes et al, Fertility and Sterility, 1994, 62/3:468–476.*
Felberbaum et al, Human Reproduction, 2000, 15/5:1015–1020.*
Olivennes et al, Human Reproduction Update 2000, 6/4:313–317 □ □.*
Felberbaum et al, Eur. J. Obstet. & Gyn. and Reproductive Biology, 1995, 61:151–155.*

(List continued on next page.)

Primary Examiner—Nita Minnifield
(74) Attorney, Agent, or Firm—Pillsbury Winthrop LLP

(57) ABSTRACT

A novel lyophilizate and method of preparation as well as the use of the lyophilizate to treat female infertility and for gonad protection. Cetrorelix is dissolved in acetic acid 30% v/v, the solution is transferred to water and freeze dried.

2 Claims, No Drawings

OTHER PUBLICATIONS

Diedrich et al, Human Reproduction, 1994, 9/5:788–791.*
Klingmuller et al, Acta Endocrinologica, 1993, 128:15–18.*
Reissmann et al, Human Reproduction, 1994, 9/5:767–769.*
Beyzarov et al, Drug Topics, Oct. 2000, 144/19:28.*
Christin–Maitre et al, Clinical Endocrinology, 2000, 52/6:721–726.*
Mettler et al, Clinical and Experimental Obstet. and Gyn., 2000, 7/2:103–105.*
Nikolettos et al, Eur. J. Obs. and Gyn. and Reproductive Biology, 2001, 97/2:202–207.*
Ortmann et al, Human Reproduction, 2001, 16/4:608–611.*
Wiklund et al, Human Reproduction, 2001, 16/8:1676–1681.*
Craft et al, Human Reproduction, 1999, 14/12:2959–2962.*
Lin et al, Human Reproduction, 1999, 14/4:885–888.*
Ludwig et al, Fertility and Sterility, 2001, 75/1:18–22.*
Felberbaum et al, Human Reproduction, 1999, 14/Suppl. 1:207–221.*
Rabasseda et al, Drugs of the Future, 1999, 24/4:393–403.*
Fraser et al, Trends in Endocrinology and Metabolism, 1994, 5/2:87–93.*
Diedrich et al, Seminars in Reprdouctive Medicine, 2001, 19/3:213–220.*
Kamischke et al., "Gonadal Protection from Radiation by GnRH Antagonist or Recombinant Human FSH: A Controlled Trial in a Male Nonhuman Primate (*Macaca fascicularis*)," *Journal of Endocrinology*, vol. 179, pp. 183–194, 2003.

Karashima et al., "Protective Effects of Analogs of Luteinizing Hormone–Releasing Hormone Against Chemotherapy–Induced Testicular Damage in Rats," *Proc. National Academy of Sciences*, vol. 85, Apr. 1988, pp. 2329–2333.

Schally et al., "Protective Effects of Analogs of Luteinizing Hormone–Releasing Hormone Against X–Radiation–Induced Testicular Damage in Rats," *Proc. National Academy of Sciences*, vol. 84, Feb. 1987, pp. 851–855.

Schally et al., "Current Concept for Improving Treatment of Prostate Cancer Based on Combination of LH–RH Agonists with Other Agents," *Prostate Cancer, Part A: Research, Endocrine Treatment, and Histopathology*, 1987, pp. 173–197.

Schally et al., "Antitumor Effects of Analogs of Hypothalamic Hormones in Endocrine–Dependent Cancers," *Proceedings of the Society for Experimental Biology and Medicine*, vol. 175, 1984, pp. 259–281.

Szende et al., "Suppression of Meiosis of Male Germ Cells by an Antagonist of Luteinizing Hormone–Releasing Hormone," *Proc. National Academy of Sciences*, vol. 87, Feb. 1990, pp. 901–903.

Yoshikazu et al., "Peptide and Antidemential Agent Containing the Same," JP2273699, Nov. 8, 1990, Abstract only.

* cited by examiner

OLIGOPEPTIDE LYOPHILISATE, THEIR PREPARATION AND USE

CROSS-REFERENCE TO RELATED APPLICATIONS

This is a divisional of U.S. patent application Ser. No. 08/468,145, filed Jun. 6, 1995, which is a continuation-in-part of U.S. patent application Ser. No. 08/198,037, filed Feb. 22, 1994, (now abandoned), which in turn claims priority to German Patent Application No. P 4305225.8, filed Feb. 19, 1993. All applications are incorporated in their entirety herein by reference.

The present invention relates to the preparation of a lyophilizate of a peptide and the use of the lyophilizate in the treatment of infertility and to provide male gonad protection.

BACKGROUND OF THE INVENTION

Cetrorelix is a decapeptide with a terminal acid amide group that is used in the form of-its acetate salt. The synthesis and some pharmacological effects are described in European patent application 299 402 (U.S. Pat. No. 4,800,191).

It should be possible to administer the active substance subcutaneously in a dose of 0.1 to 20 mg. Aqueous solutions of the decapeptide are unstable, and, therefore, autoclaving in the container used to distribute it is not possible. During conventional sterilization, using the prescribed conditions, the decapeptide tends to decompose. To obtain an injectable solution it was therefore necessary to develop a lyophilizate.

The amount of active substance in the solution to be lyophilized is, however, so small that, in low active substance concentrations, only a loose fluff results on the glass wall of the ampoule after drying the solution free of auxiliary substances, and this fluff is carried out of the vial with the stream of water vapor generated by the sublimation process. It is therefore necessary to use a bulking agent that forms a stable cake. In high concentrations, this auxiliary substance can be dispensed with. The following auxiliary substances may be considered as bulking agents: hexitols, in particular mannitol, glucitol, sorbitol, such as D-sorbitol, dulcitol, allitol, altritol (for example D- and L-altritol), iditol (for example D- and L-iditol), their optically active forms (D- and L-forms) as well as the corresponding racemates. Mannitol is used in particular, such as D-mannitol, L-mannitol, DL-mannitol, sorbitol and/or dulcitol, and, of these, D-mannitol is preferred. The hexitol used may also be composed of a mixture of the hexitols named, for example a mixture of mannitol and sorbitol and/or dulcitol. Since dulcitol is less water soluble than, for example, mannitol, the dulcitol content in the aqueous solution should not exceed, for example, 3 percent by weight. Mannitol and sorbitol, on the other hand, can for example be mixed in any ratio.

Apart from hexitol it is also possible to add other, conventional pharmaceutical auxiliary substances, such as amino acids, such as alanine, glycine, lysine, phenylalanine, asparaginic acid, glutaminic acid, leucine, lactose, polyvinylpyrrolidone, glucose, fructose, albumin and equivalent bulking agents. Urea and sodium chloride may also be used as bulking agents. The total amount of such substances in the solution which is used for freeze-drying, is for example 0–16.9 parts by weight, for example 0.1–7 parts by weight, based on 1 part by weight of cetrorelix. In the finished lyophilizate the total amount of such auxiliary substances may be up to 16.9 parts by weight, based on one part by weight of hexitol. In detail, the amount of such auxiliary substances depends on the amount of hexitol present and to such an extent that the total amount of hexitol and such other auxiliary substances in the finished lyophilizate may not be more than a maximum of 17 parts by weight, based on 1 part by weight of cetrorelix. If only 0.1 part by weight of hexitol is present in the lyophilizate, it is thus possible to have up to 16.9 parts by weight of other auxiliary substances; if, for example, 8.5 parts by weight of hexitol are present, the amount of other auxiliary substances may for example be up to 8.5 parts by weight, based on 1 part by weight of cetrorelix.

It was, however, found, during development work on the lyophilizate, that the active substance behaves in a widely variable and unpredictable manner during processing. The first batches gave good results, but it soon transpired that difficulties occurred during sterile filtration and faulty batches resulted.

It is known from the literature, for example from Powell, M. F.; Pharmaceutical Research, 1258–1263 (8)1991; Dathe, M: Int. J. Peptide Protein Res. 344–349 (36) 1990; Szejtli, J.: Pharmaceutical Technology International 16–22, 1991 that oligopeptides, particularly those with terminal acid amide function, tend to form gels. During sterile filtration this is apparent from the speed of filtration, indeed the increased viscosity of such solutions can often already be detected organoleptically. A gelatinous layer remains on the sterile filter. It is then no longer possible to prepare a medication with an exactly and reproducibly defined active substance content.

Table 1 lists various results of the first 11 batches.

The active substance contents fluctuate between 100% and 36%.

TABLE 1

Cetrorelix acetate

| Batch | Dosage | Active substance content % |
|---|---|---|
| 1 | 100 µg | 100 |
| 2 | 500 µg | 100 |
| 3 | 500 µg | 90 |
| 4 | 500 µg | 36 |
| 5 | 500 µg | 100 |
| 6 | 500 µg | 85 |
| 7 | 1 mg | 80 |
| 8 | 1 mg | 100 |
| 9 | 2 mg | 100 |
| 10 | 2 mg | 80 |
| 11 | 2 mg | 100 |

To avoid this gel formation, the literature lists the following additives which may be tried out on an experimental basis:

Organic solvents may be considered, for example acetonitrile, n-butanol, tertiary butanol, ethanol, isopropanol, octanol and benzyl alcohol. It is also possible to use salts and buffer solutions, such as acetate buffer, citrate buffer, sodium chloride, sodium phosphate, sodium EDTA, sodium bicarbonate, phosphate buffer, guanidine acetate, urea.

Polymers may also be used, such as gelatin, polyethylene glycol 600, hydroxyethyl starch, polyvinylpyrrolidone, polyvinyl alcohol. The use of amino acids, for example alanine, glycine, lysine, phenylalanine, asparaginic acid, glutaminic acid and leucine has also been described. Acids that were used were citric acid, caprylic acid, octanoic acid, hydrochloric acid, sulphuric acid and acetic acid. Physiologically acceptable surfactants that may be used are benzalkonium chloride, cetyl alcohol, bile acids, lecithins, polysorbates, Spans® and Pluronics®.

Carbohydrates and cyclodextrins such as glucose, lactose, mannitol, saccharose, alpha-, beta- and gamma cyclodextrins, hydroxypropyl-alpha- and beta-cyclodextrins, hydroxyethyl cyclodextrins and methyl cyclodextrins have already been used. These auxiliary substances were tested as filtration supporting agents to prevent gel formation.

No satisfactory solution of the problem could, however, be found. Only acidification with acetic acid showed partial success. Here, too, it was, however, always necessary to accept high filtration losses.

SUMMARY OF THE INVENTION

It was then surprisingly found that peptides having 3–15 amino acids such as cetrorelix can be easily dissolved in 30% volume/volume acetic acid. The solution is then diluted to a final concentration of 3% peptide, e.g., cetrorelix, with water for injection purposes and mannitol is added. Although it is stated in the literature that the terminal amide group hydrolyzes easily in acid medium, this was not found in the case of cetrorelix. Solutions prepared according to this method caused no difficulties during filtration. The correct amounts of active substance were always found.

Thus, in accordance with the present invention, a peptide which contains 3–15 amino acids is dissolved in acetic acid to form a solution containing 100–10,000 parts by weight of acetic acid for each part of peptide, the solution is transferred to water, and the resulting solution is lyophilized.

The filtration speed of the acetic acid solution attains values that ensure satisfactory production sequences. A general process for sterile lyophilization described in pages 557–559 of Sucker, Fuchs and Speiser (Publishers) "Pharmazeutische Technologie" 2nd edition 1991, Thieme-Verlag, Stuttgart-N.Y. A further description of the lyphilization process used is given in German published specification (DOS) 37 35 614 (U.S. Pat. No. 5,204,335).

The lyophilizate is used in the treatment of female sterility. One therapeutic process has hitherto consisted in stimulating follicle maturation using human menopause gonadotrophin and then triggering ovulation by administering human chorion gonadotrophin. The ovulation triggered thereby occurred 32 hours later. The resulting ova are available for in vitro fertilization.

A disadvantage of this treatment with agonists is the fact that up to 10 follicles mature during the stimulation phase. This elevated follicle maturation leads to hormone level peaks in the LH. These peaks result in an early stage of follicle maturation and ovulation at an unpredicted point in time. This impaired ovulation occurs in about 25% of treated cases and is a disadvantage since the cycle that displays disturbed ovulation of this kind cannot be used for the collection of ova and the entire treatment has to be repeated about 1 month later.

Another disadvantage of the conventional simulation treatment and the use of LHRH agonists in order to avoid premature LH-peaks is the long treatment duration of 4 weeks which is needed to achieve satisfactory suppression. The agonists continue to display a hyperstimulation syndrome in 1–2% of cases in which the follicle cells hypertrophy. The risk of hyperstimulation is particularly great in the case of polycystic ovaries. The hyperstimulation syndrome is a severe side effect which can lead to fatalities.

It has now been found that the antagonist cetrorelix displays the following advantages in this treatment:

Treatment with cetrorelix over 5 days is sufficient to achieve total suppression. The premature LH peaks cannot arise and the frequency of hyperstimulation syndrome should be reduced. In addition, less HMG is used in the 2nd phase of therapy, the ovulation triggering phase. This gives this in-vitro fertilization treatment a not inconsiderable cost advantage. In-vitro fertilization is, for example, used when a tube anomaly is present. To perform this treatment it is necessary to precisely monitor the cycle and to establish the time of ovulation as precisely as possible. This has hitherto only been achieved to a limited extent since preovulatory LH increase often occurred too early due to simulation with HMG/HCG, or was not maintained for a sufficiently long period. Avoidance of this premature increase is, however, of critical importance for the success-of-the treatment in order to precisely determine the time of fertilization. This reduces the physical and mental burden on the patient and makes optimum use of hospital logistics. To achieve this objective with great reliability it is necessary to suppress endogenous hormone production (LH-FSH, oestradiol) as completely as possible in order to simultaneously stimulate follicle maturation through administration of exogenous gonadotrophins (HMG/HCG) and to monitor the hormone status at any time. It is only when a sufficiently large number of follicles have been achieved (4–6), having approximately the same degree of maturation, that ovulation is triggered by administering an HCG bolus injection.

Use of an antagonist makes treatment substantially more successful and safer for the patient.

Another area of use of the cetrorelix lyophilizate according to the present invention is to protect the gonads in male patients. Male patients are pre-treated with cetrorelix lyophilizate and the activity of the gonads is reinforced. As a result, other harmful noxious agents, such as radiation therapy or treatment with cytostatics, have no or only a small possibility of affecting the sensitive tissue of the gonads.

DETAILED DESCRIPTION OF PREFERRED EMBODIMENTS

The following Examples illustrate the invention.

EXAMPLE 1

Approx. 1.5 liters of water for injection purposes are prepared in a suitable glass vessel. 210 g water for injection purposes are prepared in another glass vessel and 91.17 g acetic acid are added. The amount of cetrorelix acetate calculated (1.62–1.695 g, depending on the content of the batch used) is dissolved in the prepared 30% acetic acid with stirring. This solution is transferred to the glass vessel with 1.5 liters of water for injection purposes, 82.2 g mannitol are added, dissolved and made up to 3039 g with water for injection purposes.

| In-process checks: | |
| --- | --- |
| pH value: | 2.5–3.0 |
| Density: | 1.0213–1.0225 g/cm$^3$ at 20° C. |
| Refractive Index: | 1.335–1.345 at 589 nm at 20° C. |

The solution is sterilized by filtration through an appropriate membrane filter (pore size 0.2 µm) under aseptic conditions. 100 ml first runnings should be discarded. The filters should be sterilized with superheated steam before sterile filtration. Cetrorelix freeze-dried solution should be protected from recontamination during storage.

The solution is immediately filled into colorless injection bottles DIN 2R, hydrolytic class I under aseptic conditions and provided with sterile freeze-drying stoppers. The nominal filling amount is 2.0 ml=2.026 g.

The 2 ml injection bottles were rinsed in an injection bottle washing machine, dried with hot air and sterilized. The cleaned, freeze-drying stoppers were autoclaved. The closed injection bottles were transferred to a freeze-drying installation and frozen at a plate temperature of −40° C. Drying was carried out using a drying program with a plate temperature of −40° C. rising to +20° C. The installation is then flooded with sterile nitrogen, the bottles are closed in the installation and the stoppers secured with crimped caps.

The injection bottles are checked visually for faulty closures and outer faults. Faulty injection bottles are removed and destroyed.

Cetrorelix lyophilizate 1 mg is a white, solid, freeze-dried cake in a colorless 2 ml injection bottle which is closed with gray freeze-drying stoppers and yellow flip-off crimped caps.

EXAMPLE 2
Nonapeptide (Bombesin-antagonist)

420 g water for injection purpose are prepared in a suitable vessel and 121.56 g acetic acid are added. The amount of the nonapeptide (about 3.783 g, depending on the content of the batch used) is dissolved in the prepared 20% acetic acid and with stirring. 82., 2 niannitol are added and dissolved. This solution is sterilized by filtration through an appropriate membrane filter (pore size 0.2 μm) under aseptic conditions. The same membrane filter is used for the water for injection purpose to make up the solution to 3064 g. The filters should be sterilized with superheated steam.

| In-process checks: | |
| --- | --- |
| pH value: | 2.5–3.0 |
| Density: | 1.0232–1.0252 g/cm$^3$ at 20° C. |
| Refractive Index: | 1.334–1.344 at 589 nm at 20° C. |

The solution should be protected from recontamination during storage. The solution is filled in to sterile colorless injection bottles DIN 2 R, hydrolytic class I under aseptic conditions and provided with sterile freeze-drying stoppers. The nominal filling amount is 1.0 ml=1.022 g.

The 2 ml injection bottles were rinsed in an injection bottle washing machine, dried with hot air and sterilized. The cleaned freeze-drying stoppers were autoclaved. The injection bottles were transferred to a freeze-drying installation and frozen at a plate temperature of −40° C.

Drying was carried out using a drying programme with a plate temperature of −40° C. rising to +20° C. The installation is then flooded with sterile nitrogen, the bottles are closed in the installation and the stoppers are sealed with crimped caps.

The injection bottles are checked visually for faulty closures and outer faults. Faulty injection bottles are removed and destroyed.

The lyophilisate of the nonapeptide (1 mg) is a white, solid, freeze-dried cake in a colorless 2 ml injection bottle which is closed with grey freeze-drying stoppers and flip-off crimped caps.

EXAMPLE 3
Tripeptide (Protirelin)

143.5 g water for injection purpose are prepared in a suitable vessel and 61.5 g acetic acid are added. The amount of the Protirelin acetate calculated (equivalent to 800 mg of the peptide base) is dissolved with stirring. This solution is transferred to another vessel with approximately 1 l water for injection purpose. 109.6 g mannitol are added, dissolved and made up to 2048 g with water for injection purposes.

| In-process checks: | |
| --- | --- |
| pH value: | 2.5–3.0 |
| Density: | 1.0235–1.0255 g/cm$^3$ at 20° C. |
| Refractive Index: | 1.336–1.348 at 589 nm at 20° C. |

The solution is filled in to sterile colorless injection bottles DIN 2 R, hydrolytic class I under aseptic conditions and provided with sterile freeze-drying stoppers. The nominal filling amount is 1.0 ml=1.024 g.

The 2 ml injection bottles were rinsed in-an injection bottle washing machine, dried with hot air and sterilized. The cleaned freeze-drying stoppers were autoclaved. The injection bottles were transferred to a freeze-drying installation and frozen at a plate temperature of −40° C.

Drying was carried out using a drying programme with a plate temperature of −40° C. rising to +20° C. The installation is then flooded with sterile nitrogen, the bottles are closed in the installation and the stoppers are sealed with crimped caps.

The injection bottles are checked visually for faulty closures and outer faults. Faulty injection bottles are removed and destroyed.

The Protireline lyophilizate (0.4 mg) is a white, solid, freeze-dried cake in a colorless 2 ml injection bottle which is closed with grey freeze-drying stoppers and flip-off crimped caps.

EXAMPLE 4
Tetradecapeptide (Somatostatin)

245 g water for injection purpose are prepared in a suitable vessel and 61.5 g acetic acid are added. The amount of somatostatine acetate calculated (0.52–0.66 g, dependent on the content of the batch used) is dissolved with stirring. This solution is transferred to another vessel with approximately 1 l water for injection purpose. 109.6 g mannitol are added, dissolved and made up to 2049 g with water for injection purposes.

In-process checks:
pH value: 2.5–3.0
Density: 1.0232–1.0252 g/cm$^3$ at 20° C.
Refractive index: 1.336–1.348 at 589 nm at 20° C.

The solution is filled in to sterile colorless injection bottles DIN 2 R, hydrolytic class I under aseptic conditions and provided with sterile freeze-drying stoppers. The nominal filling amount is 1.0 ml=1.024 g.

The 2 ml injection bottles were rinsed in an injection bottle washing machine, dried with hot air and sterilized. The cleaned freeze-drying stoppers were autoclaved. The injection bottles were transferred to a freeze-drying installation and frozen at a plate temperature of −40° C.

Drying was carried out using a drying programme with a plate temperature of −40° C. rising to +20° C. The installation is then flooded with sterile nitrogen, the bottles are closed in the installation and the stoppers are sealed with crimped caps.

The injection bottles are checked visually for faulty closures and outer faults. Faulty injection bottles are removed and destroyed.

The lyophilizate (0.25 mg somatostatine acetate) is a white, solid, freeze-dried cake in a colorless 2 ml injection bottle which is closed with grey freeze-drying stoppers and flip-off crimped caps.

What is claimed is:

1. A method of treating female infertility which comprises administering, to a female undergoing controlled ovarian stimulation, an effective amount of pharmaceutical composition comprising a lyophilizate of a certrorelix solution containing 100–10,000 parts by weight of acetic acid per part of dissolved cetrorelix, thereby preventing premature ovulation.

2. The method according to claim 1, wherein the lyophilizate further comprises a bulking agent.

* * * * *